United States Patent [19]

Cox

[11] Patent Number: 5,014,908

[45] Date of Patent: May 14, 1991

[54] CONTROL CIRCUIT USING A SULPHONATED FLUOROCARBON HUMIDITY SENSOR

[75] Inventor: Karmen D. Cox, St. Peters, Mo.

[73] Assignee: Emerson Electric Co., St. Louis, Mo.

[21] Appl. No.: 441,753

[22] Filed: Nov. 27, 1989

[51] Int. Cl.[5] .......................... B01F 3/02; G05D 21/00
[52] U.S. Cl. ............................. 236/44 E; 73/336.5; 331/65; 324/71.1
[58] Field of Search ............................. 236/44 E, 44 A; 73/336.5; 331/65, 66; 324/61 R; 165/21

[56] References Cited

U.S. PATENT DOCUMENTS

| | | | |
|---|---|---|---|
| 3,942,718 | 3/1976 | Palmieri | 331/66 X |
| 4,546,916 | 10/1985 | Tsuaki | 236/44 E |
| 4,662,220 | 5/1987 | Lave | 73/336.5 |
| 4,683,904 | 8/1987 | Iltis | 331/65 |
| 4,816,748 | 3/1989 | Tazawa | 73/336.5 |

Primary Examiner—William E. Wayner
Attorney, Agent, or Firm—Polster, Polster and Lucchesi

[57] ABSTRACT

A control circuit (1) for use in a humidifier (H). A capacitor functioning as a humidity sensor (55) includes a sulphonated fluorocarbon material acting as the dielectric (57) of the capacitor. The material is sandwiched between sheets (59a, 59b) of a screen material which act as plates of the capacitor. An RC oscillator (53) has a variable frequency output and incorporates the capacitor. Changes in the dielectric value of the material due to sensed changes in humidity produce changes in the oscillator output frequency. A DC voltage is supplied to the oscillator. The amount of voltage impressed on the sensor at relatively high-humidity levels is controlled to prevent leakage currents caused when the material is exposed thereto. The generation of such leakage currents otherwise adversely effects sensor operation. Operation of the circuit to control operation of the humidifier is also described.

28 Claims, 3 Drawing Sheets

CONTROL CIRCUIT USING A SULPHONATED FLUOROCARBON HUMIDITY SENSOR

BACKGROUND OF THE INVENTION

This invention relates to sulphonated fluorocarbon humidity sensors and more particularly, to a control circuit for household or commercial appliances using such a sensor.

The use of sulphonated fluorocarbon sensors to measure humidity is known in the art. See, for example, U.S. Pat. No. 4,662,220 to Laue; or NASA Tech Briefs, Winter 1985, pages 55-56. One type sensor utilizes a sulphonated fluorocarbon manufactured by the E.I. DuPont du Nemours & Company under their trade name "Nafion". This material is a water-absorbent polymer typically delivered by the supplier in its hydrogen (H+) state. Humidity sensors using Nafion have household and commercial applications in, for example, humidifiers, dehumidifiers and air-conditioners. For these uses, the Nafion is converted from its H+ to its Na+ (sodium) state. This is done because the material in this latter state is less adversely affected by household chemicals.

Generally, humidity sensors using Nafion are incorporated as part of a control circuit for the appliance in which the control is used. While Nafion sensors work well in many appliances, there are problems with their wide spread use. It has been found that when used in high-humidity environments, the Nafion material produces leakage currents. As the voltage across the sensor increases, the leakage current begins to predominate and the Nafion starts acting as a battery. If the Nafion is placed between a stainless steel screen, for example, to create the humidity sensing element, metal from the screen begins to migrate into the Nafion, reducing its effectiveness as a sensing material. In some applications therefore, where high voltages are used, the sensor has gold plated screens or wires to prevent metal migration. While this may alleviate the problem, it is an expensive solution. Instead of having to incur this expense, it would useful and advantageous to have a lower cost alternative to reduce the above described effects of high voltage on the sensor in high-humidity environments.

A humidifier employing such a sensor also has other performance criteria which should be met. For example, it should only be operable when the unit has sufficient water. Otherwise, the unit not only does not perform its function; but also, the humidifier fan and associated components are needlessly run. And, even if the unit has sufficient water, if the wicking system of the unit is not functioning, the humidifier still will not operate as it should.

SUMMARY OF THE INVENTION

Among the several objects of the present invention may be noted the provision of a control circuit for use in household and commercial appliances such as humidifiers, air conditioners and the like; the provision of such a control circuit to employ a humidity sensor having a sulphonated fluorocarbon, water absorbent material as the humidity sensing material; the provision of such a sensor to utilize Nafion as the sensor material; the provision of the circuit to include compensation circuitry to counteract the effects of sensor operation in a high-humidity, high-voltage environment; the provision of the control circuit, when used in a humidifier, to be responsive to the water level in the unit and not operate when the level is too low; the provision of the control circuit to also be responsive to sensed air temperature as an indication of the operation of the humidifier's wicking action; and, the provision of such a control circuit to be relatively low cost and not requiring the use of gold screens or the like with the sensor material.

The invention, briefly stated, is to a control circuit for use in a commercial or household appliance. A capacitor includes a sulphonated fluorocarbon dielectric material. The material absorbs moisture which changes its dielectric value and thus allows the capacitor to function as a humidity sensor. The material is sandwiched between sheets of a screen material which act as plates of the capacitor. An RC oscillator circuit has a variable frequency output and incorporates the capacitor. Changes in the dielectric value of the capacitor, due to sensed changes in humidity, produce changes in the frequency output of the oscillator. DC voltage is impressed on the oscillator circuit. The amount of voltage impressed on the sensor, when the sensor is exposed to relatively high humidity levels, is controlled. This prevents leakage currents caused when the sulphonated fluorocarbon material is exposed to relatively high humidity. Otherwise, generation of these leakage currents adversely effects sensor operation. Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 6:
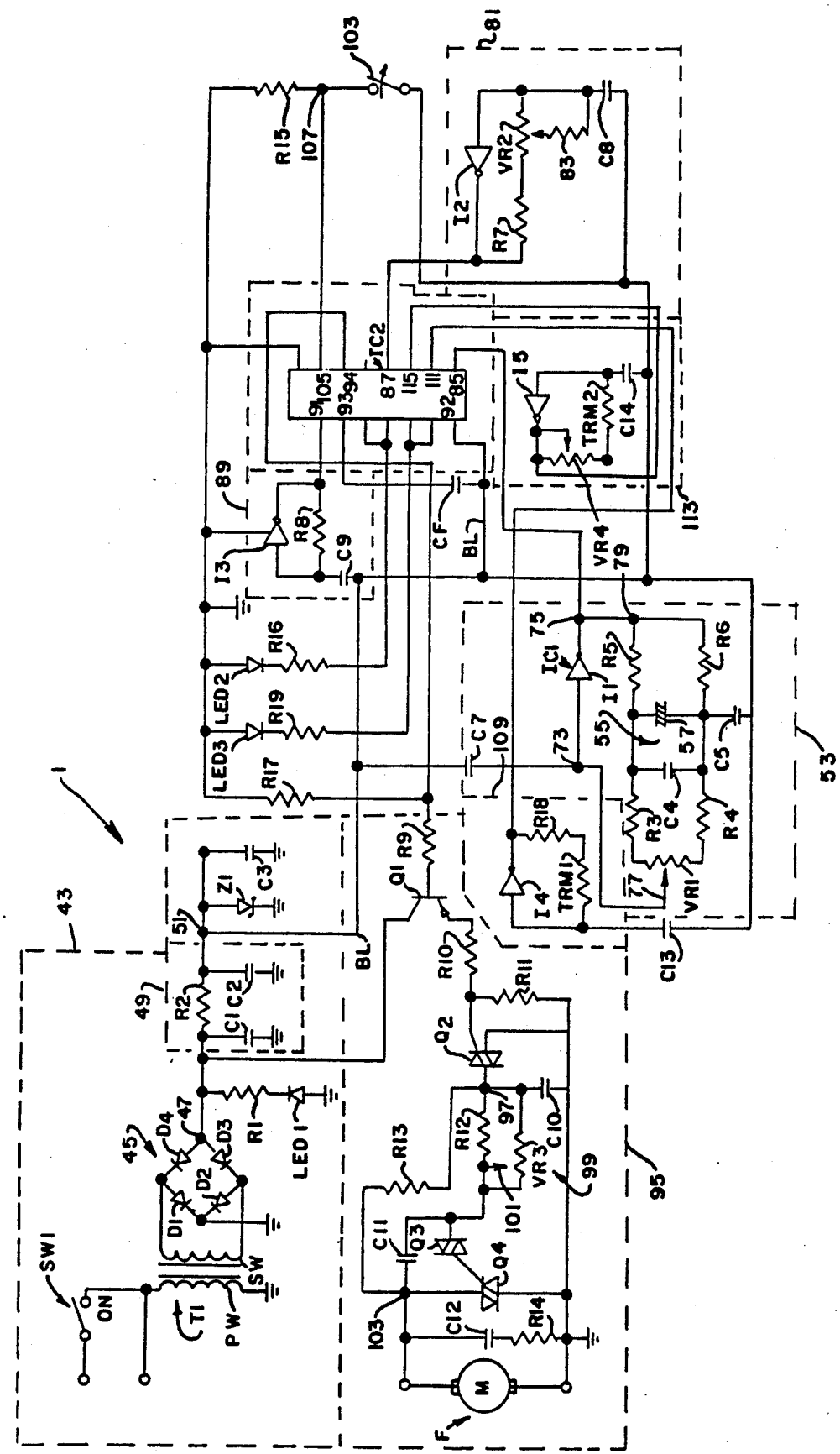

Referring to the drawings, one illustrative embodiment of a control circuit of the present invention is indicated generally by the reference numeral 1 (see FIG. 6). The circuit is used in an appliance, for example, in an air conditioner, a humidifier or a dehumidifier. For purposes of the following discussion, the use of circuit 1 in a humidifier H will be described. It will be understood, that with appropriate modifications, the circuit functions for its intended purpose equally well in other applications.

Humidifier H may be for household use or it may be a commercial appliance (i.e. a relatively larger capacity unit designed for use in commercial buildings). In either application, the appliance has an air inlet AI through which air is drawn into the humidifier unit by a motor driven fan F. A pan P at the bottom of the unit is filled with water. A wick W is suspended in the water for the water to be drawn upward into the airstream created by the fan. Air flow through the wick draws off moisture into the air which increases its humidity level and correspondingly lowers its temperature. The humidified air then leaves the unit through an air outlet AO.

Figure 1:
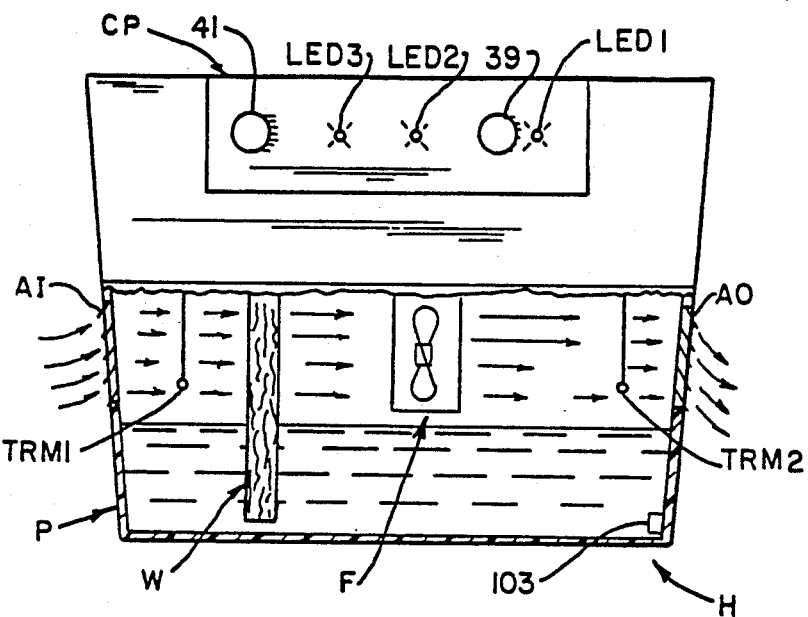
FIG. 1 is a sectional view of an appliance such as a humidifier.
Figure 2:
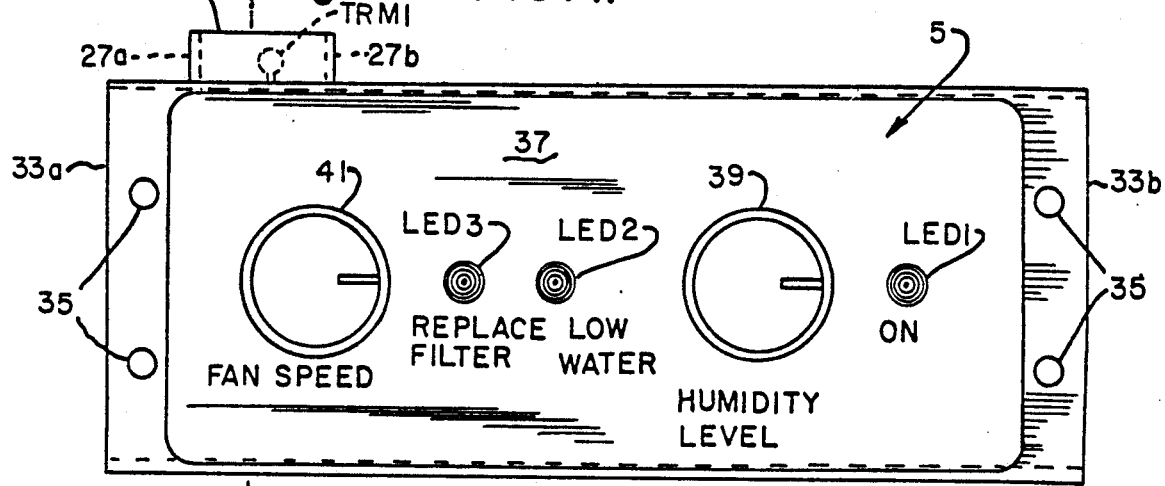
FIG. 2 is front elevational view of a control panel for the humidifier.
Figure 3:
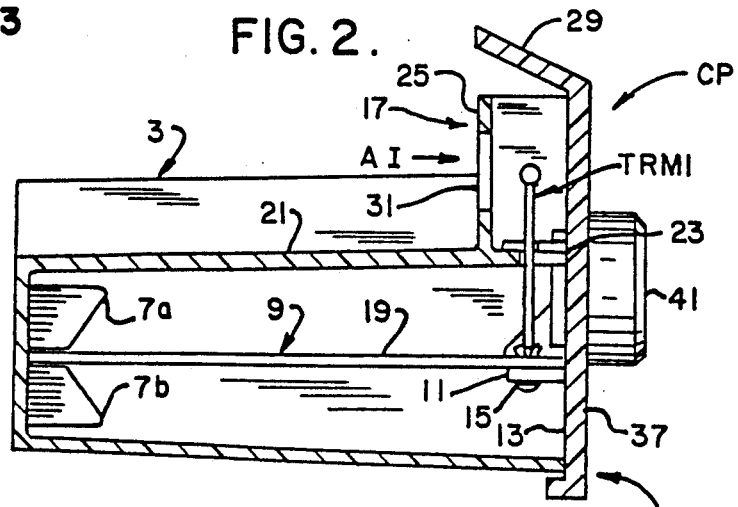
FIG. 3 is a sectional view of the control panel taken along line 3—3 in FIG. 2.

As shown in FIGS. 1-3, the humidifier has a control panel CP. This includes a rectangular shaped housing 3 whose front end is open, and a front panel or cover plate 5 which fits over this opening to close it. The housing includes upper and lower supports 7a and 7b respectively formed on the inner, rear wall of the housing. These are for mounting a printed circuit board 9 (on which control circuit 1 is implemented) in the control panel. A space equal to the thickness of board 9 separates these supports. A bracket 11 is mounted on rear face 13 of the cover plate and the front end of the printed circuit board is attached to the bracket by a rivet 15. During assembly of the control panel, the board is first attached to the cover plate and then inserted into the housing where the rear end of the board slips into the space between the upper and lower supports.

An enclosure 17 for a sensing element TRM1 (to be described hereinafter) is formed at the forward end of the housing. The element is mounted on the forward end of board 9 and has a height exceeding the distance between upper surface 19 of the board and top or roof 21 of the housing. To accommodate the element, an inset 23 is made in the housing at the forward end of the roof 21. To protect the element, enclosure 17 includes an upstanding wall 25 projecting upwardly from the top of the housing at a point slightly to the rear of the inset. The enclosure includes side walls 27a, 27b which are of the same height as wall 25 and extend forwardly of the wall to the forward end of the housing. Cover plate 5 has a height sufficient to form a fourth side of the enclosure. In addition, an ear 29 angles rearwardly from the top of the cover plate and forms a roof over the enclosure. Further, wall 25 has an opening 31 formed therein. The enclosure and opening form an air inlet AI for the humidifier and the sensing element measures the temperature of air drawn into the unit.

Cover plate 5 also has flanges 33a, 33b extending outwardly from the sides of the control panel. The flanges comprise mounting brackets for the control panel and each includes two vertically spaced holes 35 for mounting screws (not shown) or the like. This allows the control panel to be remotely located from the remainder of the humidifier unit.

Front face 37 of the cover panel has appropriate openings for mounting two control knobs, 39 and 41 respectively, and three display lights LED1, LED2, and LED3. LED1 indicates when the humidifier is turned "ON" (i.e. the LED is illuminated) or "OFF" (i.e. the LED is not illuminated). The other two LED's are signal lamps to tell the user when the water level in the humidifier is low (LED2), and when the filter wick (not shown) in the unit needs replacing (LED3). Knob 39 is used to set the desired level of humidity and knob 41 is used to adjust the speed of fan F.

Referring to FIG. 6, control circuit 1 includes an AC to DC converter 43. An "ON/OFF" switch SW1, when closed, causes AC line voltage to be impressed on the primary windings PW of a step-down transformer T1. A full-wave rectifier 45 comprising diodes D1-D4 is connected across secondary winding SW of the transformer. The rectifier has a common node 47 between the anodes of diodes D3 and D4, and the cathode of "ON/OFF" display LED1 is connected to this node through a resistor R1. A filter circuit 49 is also connected to node 47. The filter comprises a resistor R2 and capacitors C1 and C2. The capacitors are connected in parallel to the resistor at its respective ends. Rectified, filtered DC voltage is applied to a node 51 to which a zener diode Z1 is also connected. A filter capacitor C3 is connected in parallel with the zener diode. The diode is, for example, a 5.0 volt zener diode and clamps the DC voltage output of converter 43 to this value. From node 51, DC voltage is distributed to the various other components of the control circuit via a bus line BL.

The control circuit next includes an oscillatory or oscillator circuit 53 which generates an electrical signal having a variable output frequency which is a function of the air's humidity. The circuit includes a capacitance means or capacitor 55 which is exposed to air and which functions as a humidity sensor. The capacitance value of the sensor increases as the humidity increases. The capacitor uses a sulphonated fluorocarbon material 57 as its dielectric. The material, which is available from E.I. DuPont du Nemours & Company under their trade name "Nafion", absorbs moisture from the air which changes its dielectric value.

Figure 5:
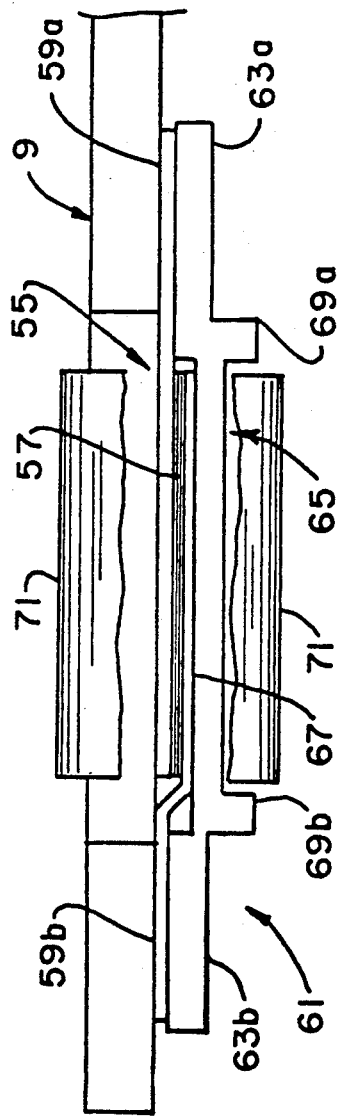
FIG. 5 is side elevational view of a portion of the board on which a humidity sensor is fabricated; and, FIG. 6 is an electrical schematic of a control circuit of the present invention utilizing the sensor.

As shown in FIG. 5, the humidity sensor is fabricated on printed circuit board 9. A sheet of material 59a, which forms one plate of a capacitor, is laid over one face of the printed circuit board. The sulphonated fluorocarbon material forming the capacitor dielectric is placed over this sheet 59a. A second sheet 59b is then placed over the exposed face of the dielectric material. A sensor cover 61 is positioned over the outer face of sheet 59b. The cover has outer flange sections 63a, 63b which fit over the respective outer portions of sheets 59a, 59b, these outer sections acting as electrical contacts for connecting the sensor into the oscillator circuit. A central section 65 of the cover has a recess 67 on its inner face in which the sensor fits. Elongate projections 69a, 69b extend the width of the cover on the respective outer edges of section 65. The projections define a mounting pad for a spring clip 71. One side of the clip fits over the sensor cover and the other side over the circuit board. The clip exerts a compressive force on the assembly to hold the sensor elements in place.

In addition to sensor 55, oscillator 53 includes an inverter I1 which comprises one portion of an integrated circuit chip IC1. Other portions of chip IC1 are utilized throughout circuit 1 to comprise various other control circuit components as is described hereinafter. Oscillator 53 is an RC oscillator. The RC components used in the oscillator are connected across respective nodes 73 and 75, at the input and output of the inverter, and include humidity sensor 55. A capacitor C4 is connected in parallel across the sensor. A voltage divider network comprising series connected resistors R3 and R4, and a potentiometer VR1, are connected in parallel across capacitor C4. The wiper arm 77 of the potentiometer is connected to node 73. In addition, sensor 55 is connected in parallel with a capacitor C5, and in parallel with resistors R5 and R6. The resistors have a common connection point 79 which, in turn, is connected to node 75. Voltage to the oscillator circuit is provided through a small value capacitor C7 which acts to eliminate high-frequency noise.

Sheets 59a, 59b are a stainless steel screen material. Heretofore, to make a sensor capacitor of a sulphonated fluorocarbon required the use, for example, of a gold plated screen material. This is because the dielectric material produces leakage currents when the sensor is exposed to high humidities. As the voltage across the sensor increases, these currents begin to predominate and the sensor material begins acting like a battery. If a stainless steel or similar screen material is used, migration of the metal into the dielectric occurs which degrades sensor performance. Capacitor C5 and resistor R6 act to control the amount of voltage impressed on sensor 55 at relatively high humidity levels. They thus prevent the leakage currents otherwise caused. At low humidities, capacitor C5 charges to the DC bias voltage and sensor 55 is exposed to approximately 1.0 volt AC maximum. As the humidity increases, the voltage across capacitor C5 increases and the voltage to which sensor 55 is exposed decreases.

The actual values of capacitor C5 and resistor R6, together with the values of capacitor C4 and resistor R5, are chosen to provide a sensor output response over a wide range of humidity values. Resistors R3, R4, and potentiometer VR1, control the maximum voltage to which sensor is exposed. The potentiometer is used to calibrate the sensor during manufacture.

Inverter I1 is a hystersis input or Schmitt trigger inverter. The output of the inverter changes state after the input to the inverter passes through a fixed voltage change. This transition in inverter output back and forth between states effectively creates a frequency output of the oscillator. Sensor 55 and its associated components produce an RC time delay for this voltage change. Since the transition of the inverter output varies as a function of sensed humidity, changes in humidity are reflected as frequency changes.

Circuit 1 also includes a second oscillator circuit 81 for generating an output having a fixed frequency. This circuit includes an inverter I2, which comprises of a portion of integrated circuit chip IC1, and an RC network connected across the inverter. The network has a capacitor C8 connected in parallel with a fixed resistor R7 and a potentiometer VR2. The wiper arm 83 of the potentiometer is adjusted by knob 39 on the cover plate of the control panel and is used to set a desired humidity level. As a result, the output frequency of oscillator 81 is a frequency corresponding to the selected humidity level.

The output frequencies of oscillators 53 and 81 are each supplied to an integrated circuit chip IC2 which incorporates a frequency comparator. The chip thus comprises means for comparing the frequencies. The frequency output of oscillator 53 is supplied to an input 85 of the chip, and the output of oscillator 81 to an input 87. A clock circuit 89 provides timing signals to the chip. The clock includes an inverter I3, which comprises a portion of chip IC1, and an RC network formed of a resistor R8 connected across the inverter and a capacitor C9 connected in parallel with the resistor. Timing pulses from the clock are provided to an input 91 of chip IC2. As noted, a DC voltage is supplied to the chip via bus line BL. This voltage is applied to an input 92 and 93 of the chip; the voltage to input 93 being noise filtered by a capacitor CF.

The frequency comparator within chip IC2 compares the frequency signals from the oscillators. When the comparison indicates the actual humidity level of the air is less than the preselected value, a control signal is supplied from an output 94 of the chip, through a resistor R9, to the base of a PNP transistor Q1. The resistor and transistor form a part of a drive circuit 95 for running fan F. The signal from chip IC2 switches transistor Q1 into conduction. The drive circuit includes a triac Q2 whose gate input is connected to the collector of transistor Q1 through a resistor R10. A resistor R11 is connected in parallel with resistor R10. This resistor and the first main terminal of the triac are each tied to electrical ground.

The second main terminal of triac Q2 is connected to a node 97. Between this node and the motor of fan F is a speed control circuit 99 for the fan. The input of a triac Q3 is connected to node 97 through a resistance network comprising a fixed resistance R12 and a parallel connected potentiometer VR3. The wiper 101 of the potentiometer is attached to knob 41 on the cover plate of the control panel and is used to adjust the fan speed. A capacitor C10 is connected between the node and electrical ground. The gate of triac Q3 is also connected to a node 103 through a capacitor C11. A resistor R13 extends between nodes 97 and 103. The first main terminal of a triac Q4 is connected to node 103, and the gate input of this triac is connected to the output of triac Q3. The second main terminal of the triac is tied to electrical ground. Fan F is connected across the first and second main terminals of triac Q4 as is a series connected capacitor C12 and resistor R14.

In operation, the user of humidifier H adjusts both knobs 39 and 41 on the control panel of the unit to respectively establish a desired humidity level and the speed at which the humidifier fan is to run to draw air through the unit. Thereafter, as the humidity level measured by sensor 55 changes, the output frequency of the signal generated by oscillator 53 changes. Oscillator 81 provides an output signal of a constant frequency which represents the preselected humidity level. The comparison logic in chip IC2 compares the respective oscillator output frequencies and when the frequency of oscillator 53 falls below that of oscillator 81, the chip supplies a command signal to drive circuit 95. The drive circuit, in turn, runs the fan, at the preset speed, so air is drawn through the unit and absorbs moisture from wick W. As the humidity level in the air increases, the output frequency of oscillator 53 changes. When the frequency of the oscillator corresponds to that of oscillator 81, chip IC2 turns off the fan drive circuit.

With respect to operation as described in the preceding paragraph, it will be understood that resistor R6 charges and discharges capacitor C5 depending upon the length of time a high or low potential output is produced by inverter I1. Resistor R5, at the same time, charges and discharges sensor 55 to the same average potential, so the average d.c. valve across the sensor is low.

For a low humidity condition, sensor 55 appears as a low capacity capacitor and thus charges and discharges rapidly with the current flow through resistor R5. Because capacitor C5 has a larger capacitance than sensor 55, the potential across it remains relatively constant. The rapidly changing potential across sensor 55 is provided as an input to inverter I1 via the voltage divider network comprised of R3, R4, and VR1. As a result, circuit 53 comprises a hysterisis oscillator operating at a high frequency. The frequency is a function of the capacitance of sensor 55 and capacitor C4.

At high humidities, sensor 55 appears as a much larger capacitance than capacitor C5. Now, the sensor does not charge and discharge as a result of current flow solely through resistor R5, but rather by the combined current flow through resistors R5 and R6. As before, the potential across sensor 55 is coupled to inverter I1 through the voltage divider network. The result is a low frequency, rather than high frequency, oscillatory circuit 53. Further, because capacitor C5 is charged and discharged, the a.c. current and voltage across sensor 55 is low.

Finally, for moderate humidity levels, the frequency of the oscillatory circuit including inverter I1 is determined primarily by the capacitance of sensor 55 as charged and discharged through resistor R5, similar to the low humidity situation. The effect of capacitor C4 is negligible in this situation. Sensor 55 will exhibit a moderate capacitance which is less than that of capacitor C5.

In addition to the various components of the control circuit described above, the circuit includes certain other features. As shown in FIG. 1, a water level switch 103 is located in pan P of the humidifier. This switch is closed so long as there is a sufficient amount of water in the pan. With the switch closed, the 5.0 volt bus voltage is provided to an input 105 of chip IC2 through the switch. As shown in FIG. 6, switch 103 is interposed in the bus line and connected to a node 107 to which chip input 105 is also connected. A resistor R15 is connected between this node and electrical ground. When the water level falls below a certain level, the switch, which is a hydraulic pressure switch, opens. Chip IC2 is responsive to this indication to provide a ground path for LED2 (via resistor R16). Voltage to the LED is supplied by bus line BL through a resistor R17. The LED now emits a low water indication light at the control panel. Because there is still water in pan P when switch 103 opens, chip IC2 allows operation of the fan to continue. However, the chip is programmed so that after a period of time, for example, two (2) hours, the chip will inhibit further operation of the drive circuit because the water in the pan is depleted. The chip will continue to inhibit operation of the fan drive circuit until pan P is filled with an amount of water sufficient to close the switch.

Figure 4:
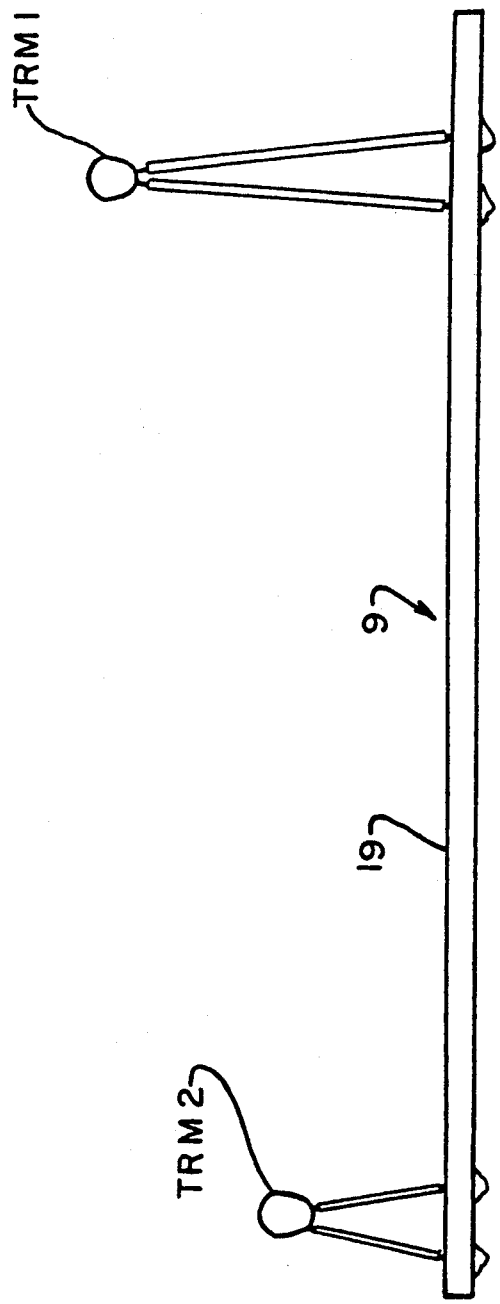
FIG. 4 is a front elevational view of a printed circuit board on which the control circuit of the present invention is implemented.

Control circuit 1 also monitors the air temperature at the inlet AI and outlet AO of the humidifier to determine if wick W is operating properly or needs to be replaced. Referring to FIGS. 1-4, a thermistor TRM1 is positioned at inlet AI. As shown in FIGS. 3 and 4, the thermistor is mounted on printed circuit board 9 and extends above upper surface 19 of the board. In addition, a second thermistor TRM2 is mounted on and extends above the printed circuit board. This second thermistor measures the temperature of the air at the humidifier air outlet. It will be understood that the outlet air temperature corresponds to the room air temperature.

An oscillator circuit 109 includes an inverter I4 which is comprised of a portion of chip IC1. Voltage to the oscillator is supplied by bus line BL through a noise filter capacitor C13. Thermistor TRM1 is connected in parallel with inverter I4 so the frequency of the output signal of the inverter varies as a function of sensed inlet air temperature. The thermistor is series connected with a resistor R18. The output of oscillator 109 is supplied to an input 111 of chip IC2.

A similar oscillator circuit 113 includes an inverter I5 which is comprised of a portion of chip IC1. Voltage to the oscillator is supplied by bus line BL through a filter capacitor C14. Thermistor TRM2 is connected in parallel with inverter I5 so the frequency of the output signal of the inverter varies as a function of sensed outlet air temperature. The thermistor is connected in series with a potentiometer VR4. This potentiometer can be adjusted for a desired room air temperature. The output of oscillator 113 is supplied to an input 115 of chip IC2.

As noted previously, when air is passed through the humidifier and absorbs water from the wick, the air temperature drops. Chip IC2 compares the frequency of the outputs of oscillators 109 and 113 and if their frequencies are substantially different, it is an indication that the wick is functioning properly. If, however, the frequency of oscillator 113 begins to approach that of oscillator 109, it means the air outlet temperature is essentially that of the air inlet temperature. I.e., wick W is dry so no moisture is imparted to passing air. The temperature difference between the inlet and outlet air temperatures at which the circuit is set to respond is, for example, 3 degrees F.-5 degrees F.

This temperature proximity signifies one of three things: (a) either a filter in the wick needs to be replaced; or (b) the wick is functioning properly but the humidifier is low on water; or (c) both the water level is low and the wick filter needs replacing.

The logic within chip IC2 first checks the condition of switch 103. If it is closed, signifying a sufficient water level, the chip allows the fan to continue running. After a predetermined period of time, for example, thirty (30) minutes, the chip checks the condition of the switch again. If it is still closed and the frequency outputs of oscillators 109 and 113 still indicate the inlet and outlet air temperatures are substantially the same, the chip provides a ground for LED3 through a resistor R19. A replace filter indication is then given on the control panel.

If chip IC2 senses that switch 103 is open, it operates as above described to provide a low water indication via LED2. If the chip has both a low water indication via switch 103, and a small temperature differential, it can also alternately open and close the ground path to each LED. This causes LED2 and LED3 to blink on and off. Since the low water indication means the unit will soon be out of water, the chip can also be programmed to allow operation of the fan for the time period mentioned previously and then inhibit further operation of the fan drive circuit.

In view of the above, it will be seen that the other objects of this invention are achieved and other advantageous results obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. A control circuit for use in an appliance comprising:

capacitance means including a sulphonated fluorocarbon material acting as the dielectric of a capacitor, the material absorbing moisture which changes its dielectric value, the material being sandwiched between sheets of a screen material which act as plates of the capacitor, and the capacitance means functioning as a humidity sensor;

RC oscillatory means having a variable frequency output and incorporating the capacitance means, changes in the dielectric value of the capacitance means due to sensed changes in humidity producing changes in the output frequency of the oscillatory means;

a source of voltage for the oscillatory means; and, means for controlling the amount of voltage impressed on the sensor at relatively high-humidity levels to prevent leakage currents caused when the sulphonated fluorocarbon material is exposed thereto, the generation of such leakage currents adversely effecting the operation of the sensor.

2. The circuit of claim 1 wherein the voltage source includes an AC to DC converter.

3. The circuit of claim 1 wherein the voltage controlling means includes a second capacitor incorporated in the oscillatory means and connected in parallel with the capacitance means.

4. The circuit of claim 3 wherein the value of the second capacitor is such that at low humidity levels it only charges to the DC bias voltage impressed on the oscillatory means by the voltage source for the voltage across the sensor to vary directly with the humidity level.

5. The circuit of claim 4 wherein the value of the second capacitor is such that when the humidity level rises above a predetermined level, the second capacitor acts to reduce the voltage across the capacitance means.

6. The circuit of claim 1 further including reference means including a second oscillatory circuit generating a fixed frequency output, means for comparing the frequencies generated by the first said and second oscillatory circuits and for producing an output based upon the comparison, and means responsive to the comparing means output.

7. In an air humidifier having an air inlet and an air outlet, means for drawing air into the inlet and through to the outlet, a source of moisture, and means for imparting the moisture to air passing through the humidifier, a circuit for controlling operation of the humidifier comprising:

means for sensing the humidity of the air and including a capacitive sensor incorporating a sulphonated fluorocarbon material as the capacitor dielectric;

first oscillator means including the capacitive sensor for generating an output whose frequency is a function of the sensed humidity level;

second oscillator means for generating an output having a fixed frequency representing a preselected humidity value;

drive means for operating the air drawing means; and, means for comparing the frequencies of the oscillator means and for providing a signal to the drive means to drive the air drawing means when the frequency comparison indicates the sensed air humidity differs from the preselected value.

8. The circuit of claim 7 including means for supplying a DC voltage to the first oscillator means, DC voltage being impressed across the sensor.

9. The circuit of claim 8 further including means for controlling the amount of voltage impressed on the sensor at relatively high-humidity levels to prevent leakage currents caused when the sulphonated fluorocarbon material is exposed thereto, the generation of such leakage currents adversely effecting the operation of the sensor.

10. The circuit of claim 9 wherein the voltage controlling means includes a second capacitor incorporated in the first oscillator means and connected in parallel with the sensor.

11. The circuit of claim 10 wherein the value of the second capacitor is such that at low humidity levels it only charges to the DC bias voltage impressed on the first oscillator means for the voltage across the sensor to vary directly with the humidity level.

12. The circuit of claim 11 wherein the value of the second capacitor is such that when the humidity level rises above a predetermined level, the second capacitor acts to reduce the voltage across the sensor.

13. The circuit of claim 9 further including means for sensing the amount of moisture available and a for providing an indication when the amount is low, the comparing means inhibiting operation of the drive means when low moisture is sensed, even though the comparison of oscillators, frequencies indicates the sensed humidity level differs from the preselected humidity level.

14. The circuit of claim 13 further including means for sensing the air temperature at the inlet and outlet.

15. The circuit of claim 14 wherein the temperature sensing means includes a first thermistor positioned at the inlet and a second thermistor positioned at the outlet.

16. The circuit of claim 15 further including a third oscillator means incorporating the first thermistor and a fourth oscillator means incorporating the second thermistor, each of said third and fourth oscillator means generating an output frequency which is a function of the respective sensed inlet and outlet temperatures.

17. The circuit of claim 16 wherein the comparing means includes means for comparing the frequencies from the third and fourth oscillator means and for inhibiting operation of the drive means if the frequencies indicate the inlet and outlet temperatures are within a preselected temperature range which is indicative of the means for imparting moisture to the air not doing so.

18. The circuit of claim 17 further including means for providing a visual indication that the moisture amount is low, the moisture imparting means is not doing so, or both.

19. The circuit of claim 7 further including a clock for the comparing means.

20. The circuit of claim 7 further including means for calibrating the capacitive sensor.

21. The circuit of claim 7 wherein the air drawing means comprises a fan and the circuit further includes means for adjusting the operating speed of the fan.

22. A control circuit for an appliance having an air inlet and an air outlet, a fan for drawing air through the appliance, a source of water, and a wick for drawing water from the source, air passing through the appliance pulling water from the wick to increase the moisture content thereof, the control circuit comprising:

a voltage source;

an air humidity sensor including a capacitive sensor incorporating a sulphonated fluorocarbon material as the capacitor dielectric;

a first oscillator including the capacitive sensor for generating an output whose frequency is a function of the sensed air humidity level;

a second oscillator whose frequency output is adjustable whereby the oscillator generates a fixed frequency output representing a preselected humidity value;

a drive circuit for driving the fan and including means for preselecting the fan operating speed;

means for comparing the frequencies of the first and second oscillators and for providing an enabling signal to the drive circuit to operate the fan means when the frequency comparison indicates the sensed air humidity differs from the preselected value; and, means for controlling the amount of voltage impressed on the capacitive sensor at relatively high-humidity levels to prevent leakage currents caused when the sulphonated fluorocarbon material is exposed thereto, the generation of such leakage currents adversely effecting operation of the sensor.

23. The circuit of claim 22 wherein the voltage controlling means includes a second capacitor incorporated in the first oscillator and connected in parallel with the capacitive sensor, the value of the second capacitor being such that at low humidity levels it only charges to the voltage impressed on the capacitive sensor for the voltage across the sensor to vary directly with the humidity level; while, when the humidity level rises above a predetermined level, the second capacitor acts to reduce the voltage across the capacitive sensor.

24. The circuit of claim 23 further including a first thermistor for sensing air temperature at the inlet and a second thermistor for sensing air temperature at the outlet.

25. The circuit of claim 24 further including a third oscillator incorporating the first thermistor and a fourth oscillator incorporating the second thermistor, each of said third and fourth oscillators generating an output frequency which is a function of the respective sensed inlet and outlet temperatures.

26. The circuit of claim 25 wherein the comparing means includes means for comparing the frequencies from the third and fourth oscillator means and for inhibiting operation of the drive circuit if the comparison indicates the inlet and outlet temperatures are within a preselected temperature range which is indicative of moisture not being imparted to air drawn through the wick.

27. The circuit of claim 22 further including means for providing a visual indication when the water level in the pan is low, moisture is not being imparted to the air by the wick, or both.

28. A control circuit for use in an appliance comprising;
a capacitor including a dielectric material, the material absorbing moisture which changes the dielectric value of the capacitor, the capacitor including a first sheet of screen material forming a first plate for the capacitor, a second sheet of screen material forming a second plate of the capacitor, the dielectric material being sandwiched therebetween to form said capacitor;
oscillator means having a variable frequency output, said capacitor being operatively connected as a component of said oscillator means, changes in the dielectric value of the capacitor producing changes in the output frequency of the oscillator means;
a source of voltage operatively connected to an input side of the oscillator; and,
means for controlling the amount of voltage impressed on the capacitor to prevent leakage current between the dielectric material and the plates of the capacitor operatively connected to said capacitor means.

* * * * *